United States Patent [19]

Freedman

[11] Patent Number: 5,176,618

[45] Date of Patent: Jan. 5, 1993

[54] SYSTEM FOR PREVENTING CLOSURE OF PASSAGEWAYS

[76] Inventor: George Freedman, 5 Brook Trail Rd., Wayland, Mass. 01778

[21] Appl. No.: 573,601

[22] Filed: Aug. 27, 1990

Related U.S. Application Data

[62] Division of Ser. No. 392,054, Aug. 10, 1989, Pat. No. 4,978,323.

[51] Int. Cl.⁵ .............................................. A61N 2/10
[52] U.S. Cl. ........................................ 600/12; 623/11
[58] Field of Search ..................... 600/9–15; 128/848, 859, 671; 623/9, 11

[56] References Cited

U.S. PATENT DOCUMENTS

| | | | |
|---|---|---|---|
| 3,926,175 | 12/1975 | Allen et al. | 128/1 R |
| 3,939,821 | 2/1976 | Roth | 128/1 R |
| 4,024,855 | 5/1977 | Bucalo | 600/12 |
| 4,053,952 | 10/1977 | Goldstein | 3/1.1 |
| 4,205,678 | 6/1980 | Adair | 128/283 |
| 4,445,501 | 5/1984 | Bresler | 600/12 |
| 4,595,390 | 6/1986 | Hakim et al. | 604/9 |
| 4,693,236 | 9/1987 | Leprevost | 128/1 R |

OTHER PUBLICATIONS

"Electromagnetic Method for In Situ Stretch of Individual Muscles", Colburn et al., *Medical & Biological Engineering & Computing*, Mar. 1980, pp. 145-152.

"A Magnetic Energy Converter for Implantable Left Ventricular Assist Devices", *Journal of Clinical Engineering*, vol. 7, No. 4, Oct.-Dec. 1982, pp. 317-322, Kovacs et al.

"The Use of Implanted Magnets to Attach A Pinna Prothesis", Abstract, Veterans Administration, Nov. 15, 1988, p. 1, Wetmore, S. J.

"Magnet Implantation for Denture and Prothesis Stabilization", Abstract, Veterans Administration, Nov. 15, 1988, p. 1, Goode, R. L.

"A Magnetic System for Urethral Closure in Females", *J. Biomed. Eng.*, 1984, vol. 6, Apr., pp. 102-106, Gruneberger et al.

"The Dental Application of Rare Earth Alloys", *Materials Australasia*, May 1987, pp. 22-23.

"Development and First Clinical Experience with a Magnetic Urethral Closure Device", *Urologe A*, (1987), 26:106-111, Gruneberger, A. D.

"The Application of Implanted Permanent Magnets in Surgery", Fedorov, V. D., pp. 72-77.

"Diagnosis, Pathogenesis, and Treatment of the Sleep Apnea Syndromes", Guilleminault, Ch., Springer-Verlag, Berlin, 1984, pp. 1-57.

"Factors Influencing Upper Airway Closure", Block et al., Chest, vol. 86, No. 1, Jul. 1984, pp. 114-122.

"Obstructive Sleep Apnea", Sullivan et al., *Clinics in Chest Medicine*, vol. 6, No. 4, Dec. 1985, pp. 633-650.

"Pathophysiology and Treatment of Obstructive Sleep Apnea", *Curr. Pulmon.*, 10:327-352, 1989, Issa et al.

*Primary Examiner*—Lee S. Cohen
*Assistant Examiner*—J. P. Lacyk
*Attorney, Agent, or Firm*—Hamilton, Brook, Smith & Reynolds

[57] ABSTRACT

An apparatus and method are provided which utilize either the attracting forces of dissimilar pole magnets, or the repelling forces of similar pole magnets, to keep passageways open in living organisms. These passageways might otherwise collapse and close involuntarily due to dysfunction, thus impeding flow of vital gaseous or liquid fluids. Embodiments are described for both permanently implanted and for removable magnets, which may or may not interact with externally attached magnets, thus maximizing the convenience of utilizing this system for the patient. A method of preventing accidental extubation is also described.

8 Claims, 7 Drawing Sheets

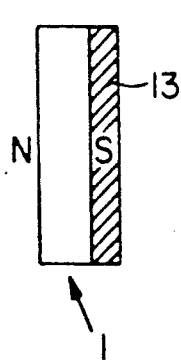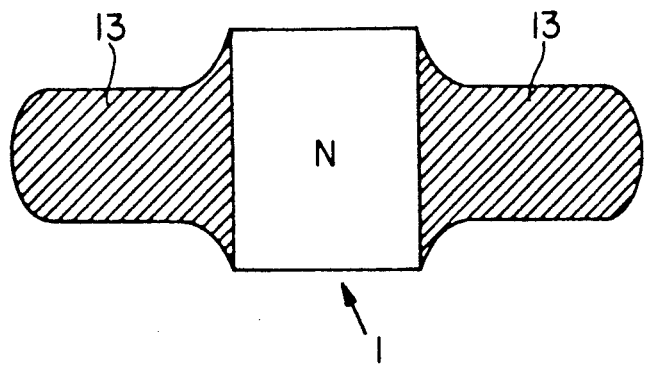
Fig. 3   Fig. 4
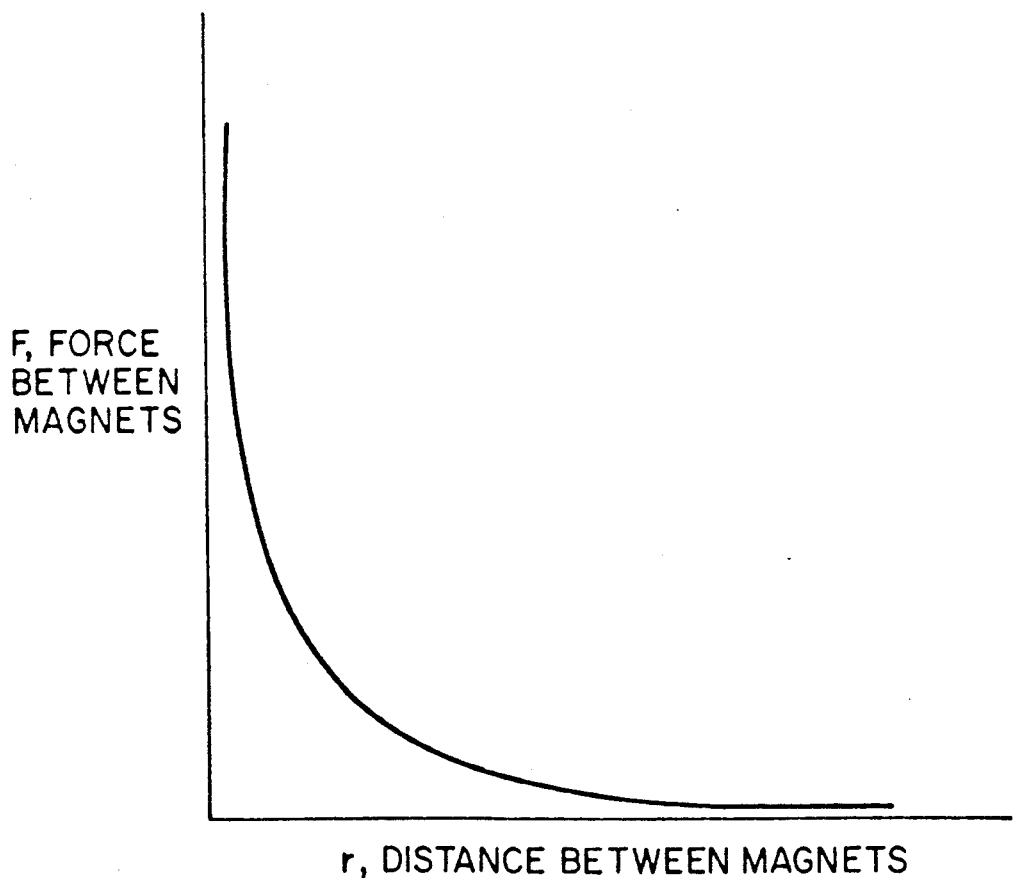
F, FORCE BETWEEN MAGNETS
r, DISTANCE BETWEEN MAGNETS
Fig. 2

SYSTEM FOR PREVENTING CLOSURE OF PASSAGEWAYS

This application is a division of application Ser. No. 07/392,054, filed Aug. 10, 1989 now U.S. Pat. No. 4,978,323.

TECHNICAL FIELD

This invention relates to prevention of discomfort, illness or death in living organisms which may be caused by the undesired and abnormal closure of a duct or channel or other passageway through which vital fluids (gases or liquids) normally flow.

BACKGROUND ART

The Physiological and Psychological Class of Problem Addressed

Before addressing specific background art, a description of the mechanism and consequence of involuntary passageway closure in living organisms is provided.

The most common and most serious dysfunctions caused by the involuntary closure of a passageway in humans occur in a debilitating and life-threatening mode in the disease known as "sleep apnea" and as an inconvenience (in aesthetic and/or psychological senses in various degrees) for those afflicted with severe snoring. There are other human and animal afflictions also connected with the involuntary closure of vital passageways to which techniques used to alleviate or cure apnea may also pertain.

In the case of sleep apnea, what occurs is an involuntary closure of a portion of the air passageway, or windpipe (also called the "airway"), that connects the mouth to the lungs and digestive system. The upper portion of the airway (the "upper airway") consists of two passageways, the nasal airway and the oral airway. Portions of the upper airway just back of the tongue are known as the soft palate, the hypopharynx, etc. Below the tongue, these two passageways merge to become a single passageway. Portions of this lower single passageway are known as the throat, the gullet, the trachea, the pharynx, the larnyx, the thorax, the esophagus, etc. Closure commonly occurs when the patient sleeps, because then his or her muscles are in a condition of minimum tenseness, indeed in the condition of relaxation associated with sleep. In those people prone to sleep apnea, there is a tendency for a portion of the inner walls of the air passage, generally in the region just back of the tongue, to become so limp and relaxed as to have a tendency to "flap shut". At that instant, the air passage is blocked, breathing stops, air movement to the lungs ceases, and the patient begins to choke. He or she awakes in a state of panic, gasping for breath, which resumes as the throat tissues tense and tighten, thus "unflapping" the closure and thus unblocking the air passage.

The patient then resumes sleeping, but another apneic attack generally follows. For those severely afflicted, there may be as many as eight episodes per hour. When these conditions persist, patients are at best constantly drowsy during the day due to constant waking up during the night, or at worst, develop heart conditions which lead to heart attacks.

There are two locations in the upper airway where apneic episodes may occur. The rates of incidence in both locations are about equal, so that they are equally important. The first location is at the soft palate at the rear of the tongue, where it makes a boundary with the nasal airway. This may flap shut against the posterior pharyngeal region which makes up the rear wall of the throat. The second location is lower down at protruding tissue, known as the hypopharynx, in the region where the nasal and oral airways merge. It, too, can flap shut against the posterior pharyngeal tissue. The hypopharynx is integral with the subglottal tissue which moves with it as it flaps shut.

People most prone to sleep apnea are generally overweight and/or with receding jaws. Some animals, especially the bulldog and the Pekingese, are prone to sleep apnea. This accounts for the fact that bulldogs are characterized as "sleepy".

Snoring is actually a mild form of sleep apnea in that total closure and blockage of air movement does not occur, but partial blockage does. Acoustical vibrations are then set up, not dissimilar from those generated in the mouthpieces of brass musical instruments, like the trumpet or trombone. These resonate and are amplified and fortified in the throat and nose chamber and emerge as the unpleasant sounds we know as snoring.

Some authoritative references on the subject of sleep apnea are Guilleminault, C., "Diagnosis, Pathogenesis, and Treatment of the Sleep Apnea Syndromes", Springer-Verlag, Berlin 1984. Block, A. J., et al., "Factors Influencing Upper Airway Closure", CHEST, Vol. 86, No. Jul. 1, 1984, p. 114, and Sullivan, C. E., et al., "Obstructive Sleep Apnea", Clinics in Chest Medicine, Vol. 6, No. 4, December 1985, p. 633.

Various procedures and devices have been developed for the mitigation of the effects of apnea. These are described below:

a. Surgery

Since the involuntary closure occurs most frequently in the region of the air passage just back of the base of the tongue, it is common to remove a portion of the fleshy inner wall of the air passage in that location. This must be done while taking care not to remove an excessive amount of tissue, since the air passage must remain whole and "air tight" for breathing.

The situation is complicated by the fact that there are several functions, in addition to air conduction for breathing, which must also be fulfilled by the airway. Those additional roles, involving muscular action in the region, must not be compromised. For example, this passageway also participates in swallowing food and drink and in establishing the quality of the voice in talking and singing. Consequently, the removal of the tissue often still leaves enough flabby fleshy structure, so as still to "flap shut" during such a condition of relaxation as occurs in sleep. Thus, the success record of surgical measures is mixed at best.

While for some patients, in the near term, the desired results in alleviating apnea without damaging other throat functions are achieved surgically, with the passage of time, sleep apnea often reappears. And, in many cases, no improvement is achieved as a result of this surgical procedure. Furthermore, in all cases, there is the risk and discomfort associated with major surgery.

b) Nasal Continuous Positive Airway Pressure (CPAP)

Good success in alleviating, without curing, sleep apnea has been achieved by the application of a simple hydraulic principle. It is that a flexible tubulation, which is what a human or animal air passage is, can be kept from collapsing if an internal pressure greater than the pressure on its external surface can be maintained within itself. In effect, it becomes a pressure vessel. This has been shown to be achievable, without recourse to modifying the passageway itself as with surgery, by attaching a nose mask to the face of the patient, which in turn is attached by a tubular conduit to a pump system. What is then achieved is a closed hydraulic (pulmonary) system of which the living air passage forms one integrated part. The pump is electrically energized and through the period of sleep, continuously generates positive air pressure (2-12 cm of pressure above ambient), enough to keep the air passage from collapsing, as it otherwise might.

A company which has pioneered in and markets this device is Respironics, Inc. of Monroeville, Pa.

The CPAP has been a boon to apnea sufferers, but it has certain disadvantages. It depends on being plugged into an electric system and damage to the sleeping patient can occur in the event of a power failure. It is an "active" device, in that there is no escaping the constant noise of motor sound. Most negatively, it requires the wearing of a face mask by the patient. This is a constant inconvenience, inhibiting normal body movements during sleep, as well as connubial satisfaction with a sex partner.

There are numerous literature references on CPAP, of which a representative is: F. G. Issa and J. E. Remmers, "Pathophysiology and Treatment of Sleep Apnea in Current Pulmonology", Vol. 10: Ed. Daniel Simmons, Yearbook Medical Publishers, Inc., 1989, pp. 327-352.

Various other mechanical and electrical means have been utilized to control passage of fluids in ducts and passageways in humans and they form a second category of prior art. They differ from the methods of passageway control, described above, in that they deal not with involuntary passageway closure, but rather, with undesired involuntarily staying open of the passageway when closure is required. Those that pertain here are associated with the use of magnets and are described below.

c) Substitution for Sphincter and Sphincter-Like Action

Living organisms make provision for both voluntary and involuntary control of movement of fluids and solids by use of strategically located muscles. The class of muscle that controls the passage of feces and urine is the sphincter, which is a noose-like muscle surrounding the passageway and which by tensing or relaxing can cause a region of the passageway to be either open or closed. For those who have lost sphincter function, it is possible to approximate at least the "closed" mode of the noose function. This is achieved by the placement of a pair of opposing pole magnets or of a pair one magnet and an element made of a ferromagnetic material, like iron. In either case, attracting magnetic forces cause these magnetic materials to move in the direction of each other, at the same time squeezing or clamping shut the tissue of the passageway which separates them.

These devices differ from living sphincters in that while they are capable of closing a passageway with positive force, they do not have the capability of applying similar but opposite force to compel a passageway to open. There are various design reasons for this, the most important of which is the fact that one magnet element of the magnet pair is inserted into a body aperture, or surgically implanted, while the other is placed externally in a crucial position on the outside skin and manually manipulated by the patient when the equivalent of sphincter closing is required. Removal of the external magnet removes the clamping force and the passageway opens by virtue of its own elasticity.

Numerous patents and technical papers may be found in the prior art relating to innovations and research into devices and methods based on noosing or clamping, as well as attaching, which function by utilizing mechanical forces resulting from magnetic fields generated by magnets correctly designed and oriented for these purposes. For magnetic closure action on ducts and passageways, the following patents have issued: Goldstein U.S. Pat. No. 4,053,952; Allen U.S. Pat. No. 3,926,175; Roth U.S. Pat. No. 3,939,821 and Hakim U.S. Pat. No. 4,595,390.

d) Related Other Magnet Applications in Living Organisms

There are many other methods and devices based on use of magnets in living passageways or tissues. Applications include attachment, muscle exercise and pumping.

1. Attachment

The literature is replete with articles describing permanent magnets used for attachment of prothesis into or onto the body, such as dentures and artificial ears and holding plugs in place in urinary passages, etc. Patents describing systems and methods for attachment of external items, such as a colostomy bag or rectal or vaginal plugs are: Adair U.S. Pat. No. 4,205,678 and Leprevost U.S. Pat. No. 4,693,236.

2. Muscle Manipulation

A unique application is described in a paper by T. R. Colburn, et al., "Electromagnetic Method for In Situ Stretch of Individual Muscles", *Medical and Biological Engineering and Computing*, March, 1988, p. 145, in which an implanted magnetizable metal (not a magnet) can be made to pull or push a muscle by being placed in a suitable external magnetic field generated by an external electromagnetic coil.

3. Internal Motors and Pumps

Another class of magnet applications, that of internal motors, is represented by S. G. Kovacs, et al., "A Magnetic Energy Converter for Implantable Left Ventricular Assist Devices", Kovacs, et al., *Journal of Clinical Engineering*, Vol. 7, No. 4, October-December, 1982, pp. 317-322, in which an electromagnetic field is used to activate a heart pump.

All these cited patents and systems make use of the forces of magnetic attraction to achieve attachment or motor-like action or closing action for an organic passageway.

SUMMARY OF THE INVENTION

The present invention discloses a method and device which averts the unwanted stoppage of the flow of vital fluids in animals and humans by ensuring that living passageways, prone to involuntary closure, are prevented from collapsing and closing.

In one embodiment, a small permanent magnet is implanted into a selected region of the passageway tissue. The implanted magnet moves to eliminate airway closure of the passageway through interaction with an external adjacent attached magnet. The internal magnet is implanted, or affixed, in "soft" frontal (anterior) tissue of the tubular airway wall between the mouth and the entrance into the larynx, at or near the epiglottis, opposite "hard" or rigid tissue at the rear (posterior) of the airway. The external magnet is oriented in polarity to attract the internal magnet and is worn in a position adjacent and nearly opposite the internal magnet on the external front wall of the larynx beneath the chin near the "soft" tissue. The opposite polarity magnetic forces produced by this arrangement cause the two magnets to attract and prevent the soft tissue from flapping shut against the more rigid rear wall.

In an alternate embodiment, two or more magnets are internally implanted, or affixed about the airway. Two such magnets are oriented in polarity so as to repel each other and are disposed on opposite walls of the airway. One is located on a "hard" tissue wall and the other on a "soft" tissue wall, at or near the epiglottis. The repelling force prevents closure of the airway. A third magnet is used to stabilize the other two and prevent occurrence of mechanical metastability, which would cause the air passage to be closed, instead of opened by the two magnets.

In yet another embodiment, a method and apparatus for prevention of accidental extubation of endotracheal tubes is provided which consists of a magnet incorporated into the wall of the endotrachael tube which faces the front of the throat. Another magnet with polarity, such as to attract the first magnet, is placed into a neckband which is so placed as to face the first magnet. The tube is thus held and prevented from accidental extubation with the same retentive force as is normally achieved with conventional systems using straps.

The above, and other embodiments of the invention, will now be described, in detail, with the aid of the drawings.

BRIEF DESCRIPTION OF THE DRAWINGS

FIG. 2 is a plot of magnetic force versus distance between magnets.

FIG. 3 is side view of a magnet extender in accordance with the invention.

FIG. 4 is a top view of the extender of FIG. 3.

DETAILED DESCRIPTION OF THE INVENTION

I. Single External Magnet Embodiment

A system consisting of a single implanted magnet which moves to eliminate airway closure (an apneaic episode) through interaction with an external attached magnet will now be described in connection with FIG. 1.

Figure 1:
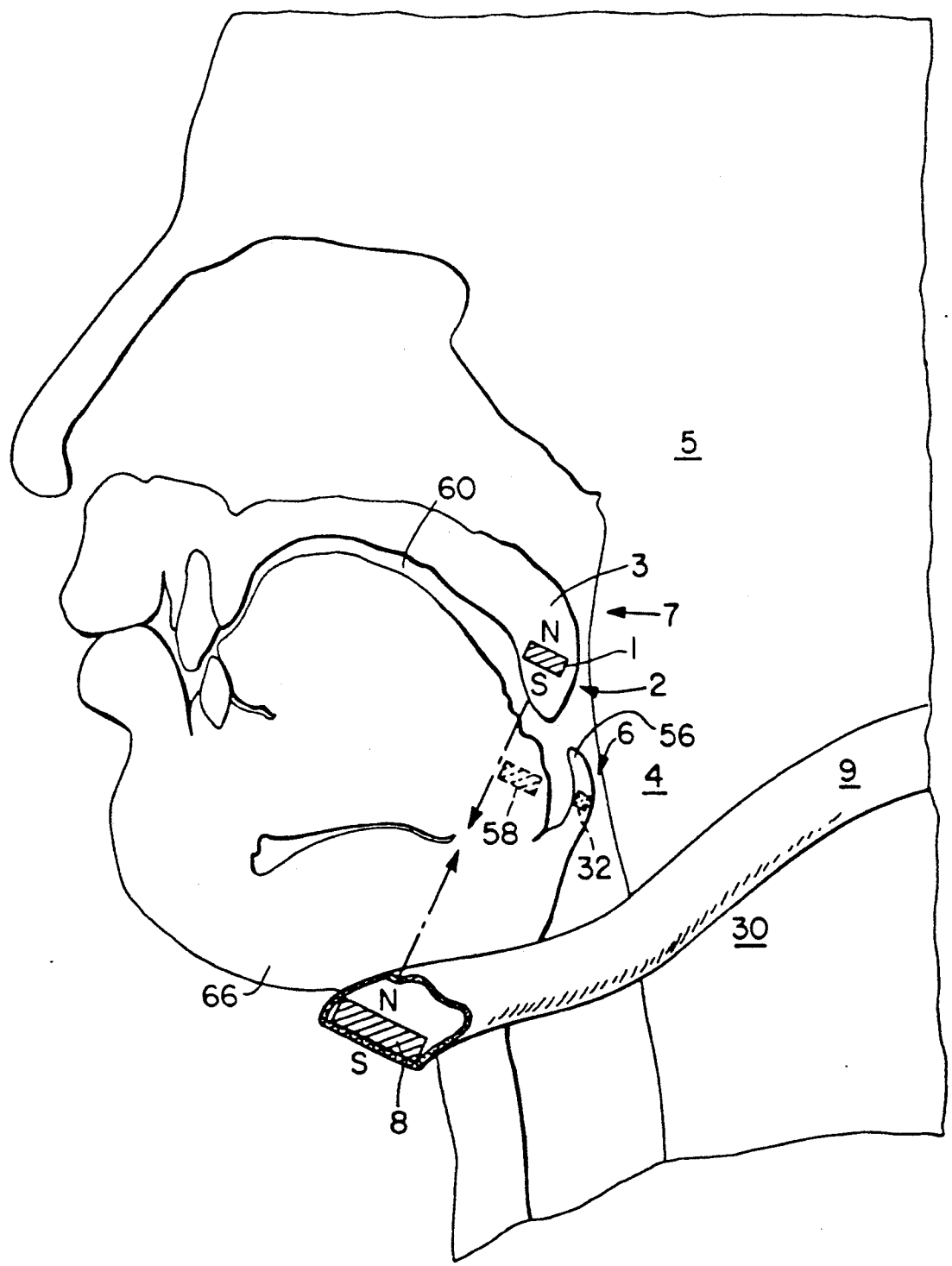
FIG. 1 is an anatomical schematic sectional view of the airway of a patient with a first embodiment of the invention illustrated.

In FIG. 1, internal magnet 1 is implanted in a location adjacent the nose airway 2 most applicable for a particular patient, such as in an inner wall of the soft palate tissue 3 in the region between the larynx 4 and nasopharynx 5 above the epiglottis 30. This is across the airway 2 from hard tissue which makes up the opposing posterior pharyngeal wall 7 of the nasal airway 2. Hard tissue is essentially rigid. Internal magnet 1 has well-defined parallel pole faces, labelled "N" and "S", one of which "S" is pointed outward and downward so as to directly "oppose" the north pole N of external magnet 8. Magnet 8 is attached to the outer skin of a patient with means such as a neckband, or chin strap, 9, which extends beneath the patient's chin 66.

Magnet pole orientation is illustrated by the arrows and results in an attraction force between the implanted magnet 1 and external magnet 8. The result of this attraction force is to move anterior nasal airway wall 3 outwardly and in a direction opposite to that of airway closure to prevent occurrence of apnea.

Force fields between magnets 1 and 8 act to keep the flabby tissue of the anterior portion of the front wall 3 of the nasal airway 2 from flapping shut against the more rigid rear wall 7. That wall's rigidity is such that it can be reckoned as unmoving, making it necessary only to control the movement of the inner wall 3. The implanted magnet 1 is sufficiently small as not to be noticed by the patient during waking or sleeping hours, or when eating or speaking.

In the other most common case of apneic closure, at the location where the oral and nasal airways merge (at 6) the magnet 1, still with the same magnetic pole orientation, may be relocated to either 58 or 32 (as shown in dotted lines) depending on the individual patient's throat structure.

The force which is required to keep the airways 2 or 6 open is known to correspond with an internal incremental air pressure in the order of 5 cm of air, as has been determined by the CPAP pump pressure system. The amount of force in that system has been shown to be tolerable and not sufficient to interfere with sleep. 5 cm of pressure can be calculated to be expressed as 33 grams per inch square, a force easily exerted by a pair of small magnets as they approach each other. Such magnets are utilized and designated as 1 and 8 in FIG. 1. Preferably, state of the art magnets of the rare earth type, examples of which are of the classes of samarium cobalt and neodymium iron should be used. They have energy products in the range from 18 million to 35 million gauss/oersteds, values which make possible large forces of attraction or repulsion for magnets of very small mass.

It is known that there is an approximate inverse-cube law relationship for either attracting forces (opposite poles facing each other) or repelling forces (similar poles facing each other) between pole faces of permanent magnets. The forces increase rapidly as the magnets move closer to each other; this may be expressed as:

$$F = cMM'/r^3 \qquad \text{Equation 1}$$

where M and M' are the magnetic dipole moments of the magnets which are separated on centers by a distance, r, and c involves the physical constants.

This inverse cube relationship between force and distance may be schematically represented in the form of the graph of FIG. 2.

Thus, depending on the embodiment (those given here choose either attracting or repelling, or a combination of these), the presence of the magnets results in markedly increasing resistance to airway wall collapse and closure, as the airway walls approach each other. Forces for final closure will never exceed counteracting magnet forces, that is, a certain amount of open passageway clearance will always be maintained.

The implanted magnet may be coated with one of the accepted polymeric materials used to coat such metallic implants as heart pacemakers, such as a urethane or silicone. This will encapsulate and seal the magnet and render the assemblage compatible with living tissue and fluids, i.e., biocompatible.

As a result of its small area, the internal magnet 1 acts on a wall of the airway almost as though it is pressing at a point contact. That region of contact, and thus the region that is inhibited from collapsing, can be effectively extended by a structural element attached to the magnet and flush with its pole face. Such a device is illustrated in FIGS. 3 and 4 as item 13. Extender 13 is a semirigid polymer structure which may be attached to the internal magnet 1 for the purpose of increasing the area over which its force can be applied to airway wall. It is shaped to conform to the inner contour of the airpipe at location of contact. It is made of a suitable polymer, such as a silicone compatible with living tissue and fluids, in accordance with the state of the art.

II. Non-External Magnet Embodiment

A system consisting of a multiple magnet array, each element of which is implanted with the result that no external magnet is required to be attached, shall now be described in connection with FIG. 5.

Figure 5:
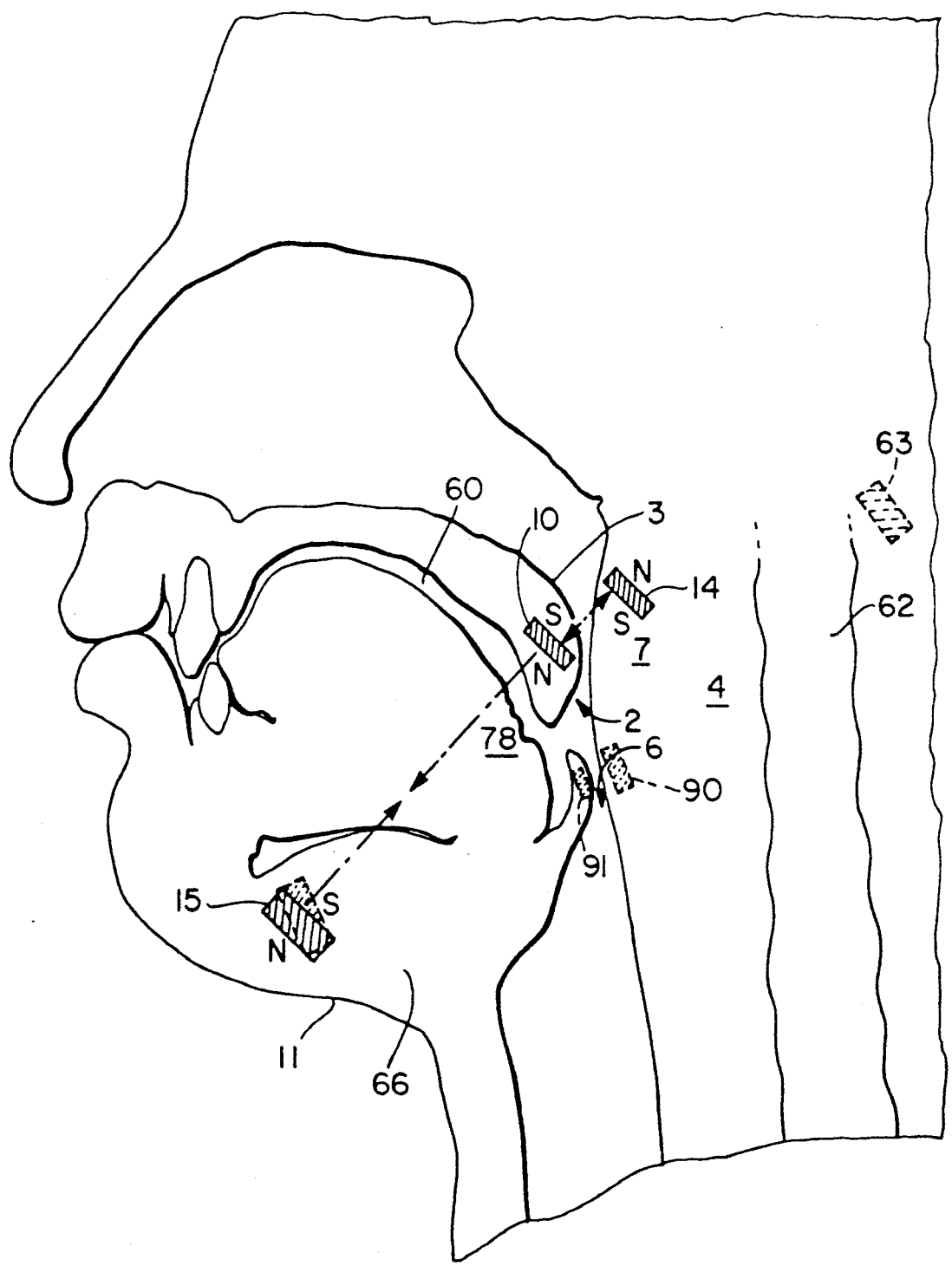
FIG. 5 is a schematic sectional view of a patient with an alternate embodiment of the invention.

In FIG. 5, an array of implanted attracting magnets are shown which repel each other (illustrated by the arrows) and which thus eliminate airway closure without the use of external magnets. This embodiment is also used where one wall of the passageway is rigid and the other is soft. Implanted primary magnet 10 is located as in the embodiment of FIG. 1; it is supplemented, however, by primary magnet 14 in rigid wall 7 and by stabilizer magnet 15 outside of the airway, but implanted beneath front skin 11 of chin 66. The expression "primary magnet" is used to designate those magnets which generate the force which is expressed against passageway walls to inhibit closure. The term differentiates such magnets from those that have a secondary role, such as the "stabilizing magnets" described below.

As indicated in FIG. 5, it is possible to dispense with the inconvenience of attaching an external magnet at the cost of implanting additional magnets which operate to eliminate the need for such an external magnet. The nasal airpipe 2 is kept from closing by the fact that in this embodiment, there are now two implanted primary magnets 14 and 10, which are oriented so as to repel each other because their similar magnetic poles face each other (as in north pole facing another north pole).

This arrangement brings with it the danger of undesired primary magnet behavior of mechanical instability, or "metastability". Metastability can be eliminated by implantation of a third magnet, known as the "stabilizing magnet" 15 which operates to stabilize the system.

Magnets 10 and 14 may be located further down at 90 and 91 (as shown in dotted lines) so as to face each other across passageway 6 for the case where the susceptibility to attack is in that region. Magnet 15 will remain at about the same location, but will be slightly tilted from the nasal airway case, so as to line up with magnets 90 and 91, as shown in phantom.

When any magnets are used in an arrangement of similar poles facing each other, a condition of mechanical metastability obtains, as contrasted to the stable condition which occurs when opposing dissimilar poles face each other and the magnets have no tendency to move in any way other than directly at each other. In the metastable case, the magnets, and especially the smaller one if they are of different size, attempt to rotate 180°, so as to reverse the orientation of the smaller one to the position wherein dissimilar poles face each other.

Figure 6:
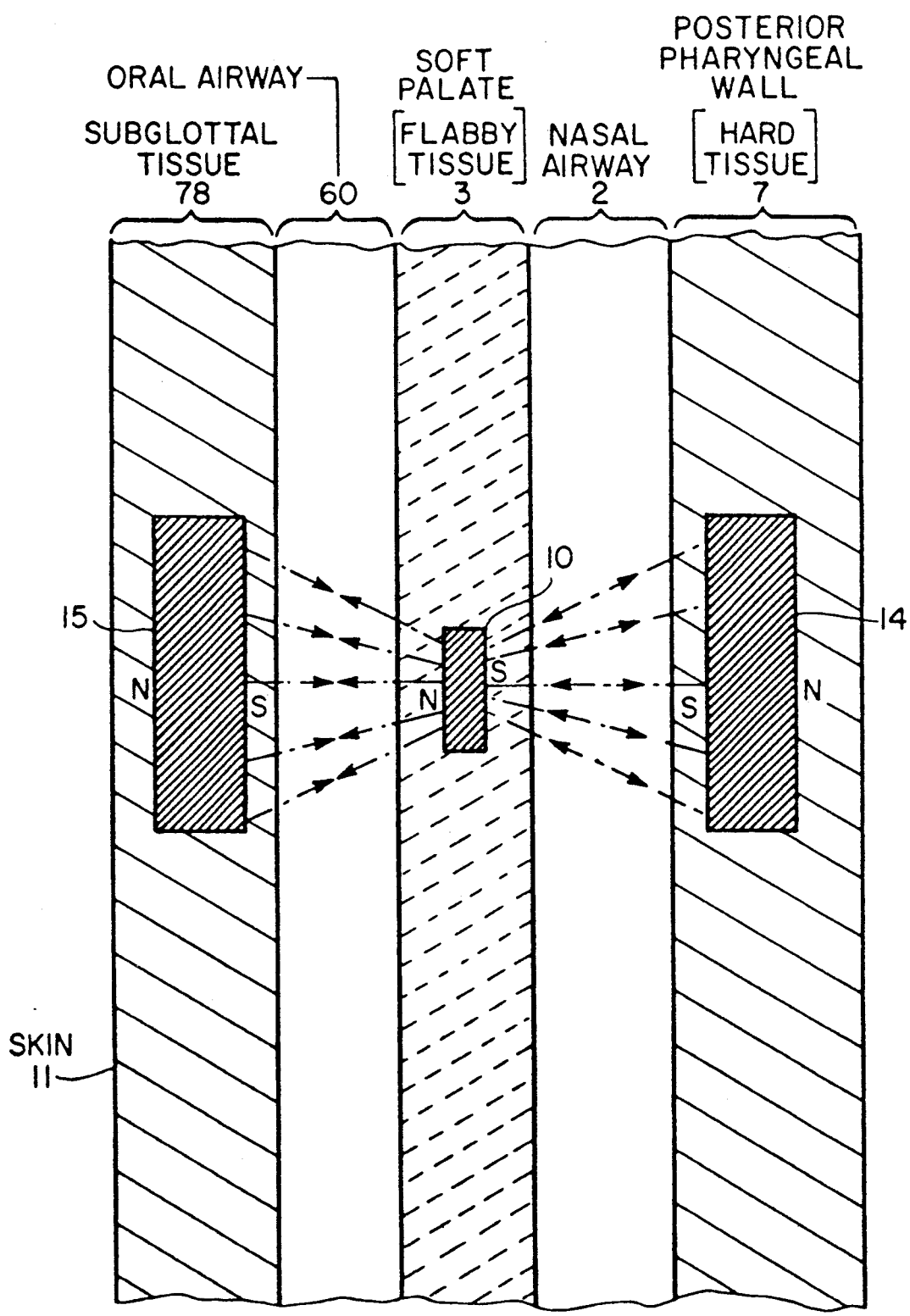
FIG. 6 is schematic representation of the force fields in FIG. 5.

Without the stabilizer magnet 15, it is possible, as a result of being in a metastable condition, for magnet 10 to twist the flabby soft tissue in which it is imbedded with it and then to become attracted to magnet 14, rather than to be repelled by it. Should that occur, the possible consequence is exactly the opposite of what is desired. Closure may then be forced to happen, and may even then be life threatening. As shown in the force field diagram of FIG. 6, it is the function of the stabilizing implanted magnet 15 to counteract this tendency, since it acts in the stable attracting mode (dissimilar poles facing), to keep magnet 10 in its original orientation. It makes the rotation impossible because it operates to exert a stabilizing force on magnet 10 and, at the same time, reinforces the repelling forces of the pair 14 and 10 because its attracting force acts in the same direction (to keep the airway open).

Figure 7:
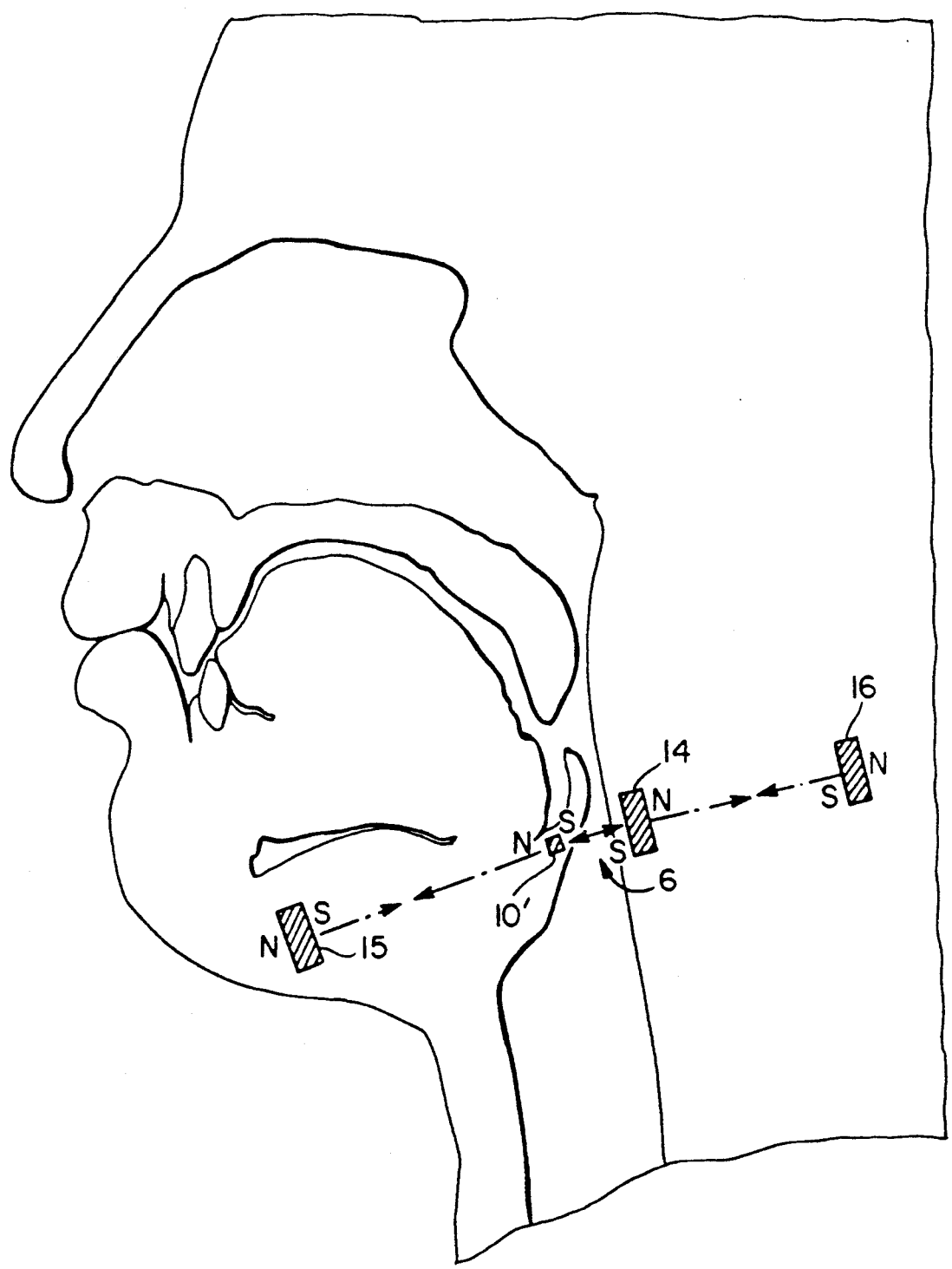
FIG. 7 is a schematic sectional view of a patient with another alternate embodiment.

Magnet 14 may be located in one of two places. Either as shown in FIG. 5, in front of the spinal column 62, or behind it, under the skin of the back of the neck at 63, as shown in phantom.

Where neither wall of the airway is rigid, as in FIG. 7, the implantation of a second stabilizing magnet 16 is required. This then serves the purpose of providing stabilization of magnet 14 in the same manner as magnet 15 stabilizes magnet 10 in Embodiment 2. In this embodiment, both 10' and 14 require stabilization. Another example of both walls being soft and flabby may occur when the soft palate in the roof of the mouth participates in the undesired closure. This embodiment is applicable in that case, as well.

III. Non-Implant Embodiment

A removable, reusable, magnet "pill" system, which makes implantation surgery unnecessary, will now be described in connection with FIG. 8.

This is applicable in only the second apneic incident mode wherein closure takes place at the lower location 6, where the oral and nasal airways merge.

Figure 8:
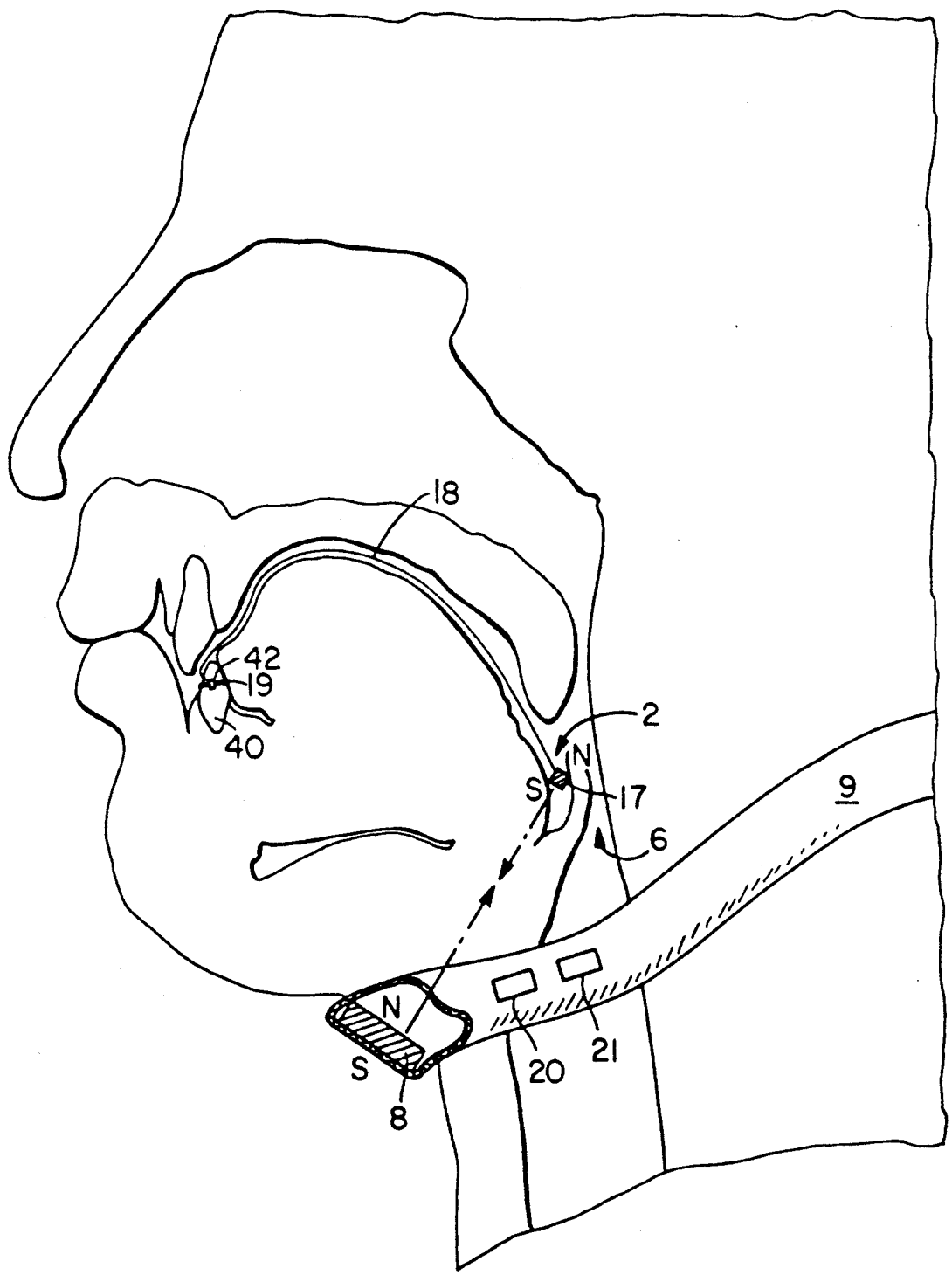
FIG. 8 is a schematic sectional view of a patient with a further alternate embodiment.

In FIG. 8, a dangling magnet 17, which is attached to one end of a thread 18, like dental floss, is shown after having been swallowed by the patient as though it were a pill. The other end of the thread is anchored to a loop 19 bonded to a tooth 40 by an orthodontic loop. Instead of implanting a magnet, such a magnet 17 is literally swallowed by the patient. It is kept in the airway 2 at the correct level by virtue of the fact that it is fastened to a fine, but strong, thread 18, the other end of which is fastened to a tooth 40, preferably a rear molar. Fastening can be accomplished with a small loop 19 to which the thread is hooked or tied. That loop, in turn, is permanently attached to the tooth by a conventional orthodontic band 42.

With practice, the patient learns to swallow the magnet, which is smaller than an aspirin tablet, and to allow it to stay in place without gagging. When external magnet 8 is affixed to the neck with neckband 9, the pill magnet 17 immediately feels the magnet force field of the magnet and rotates into its stable position of dissimilar facing poles. As shown in FIG. 8, if the external magnet 8 presents a north pole face to the airway, the pill magnet will rotate to present a dissimilar (south) pole face to it. The consequence is that the airway wall is thus pulled in the direction of the external magnet and the airway is kept from involuntarily closing.

The patient may now retire and sleep through the night without hazard of an apnea attack. In the morning when he/she awakes, the flabby tissue tenses as a result of this awakening and no apneaic attack will occur. The patient now manually pulls back the pill by pulling on the thread and disengages it from the tooth loop. He/she also takes off the attached magnet and its neckband. The described process is then repeated every time the patient again retires in order to sleep.

Although this is a regimen which the patient must go through daily, it is a simple one and far less cumbersome and unpleasant than that of attaching a CPAC face mask and pump.

IV. Electronic Sensing

An electronic sensing system for indicating and monitoring of magnet/breathing variables will now be described in connection with the invention.

The electronic system shown in FIG. 8 is a sensor, the sensing means of which is a magnet field sensitive element, such as a Hall Effect device. It is a battery powered solid state circuit 20 with a readout means 21 to indicate that magnetic locking has occurred. This electronic system is held in place by a simple attachment to the body, like a neckband 9.

Since it is possible to project a magnetic force into a living organism, in order to cause a change in function of internal magnets or ferromagnetic material, merely by attaching an external magnet to the body, such as magnet 8, then it follows that a manifestation of that force can be detected and, in that sense, become a sensing means. Magnetic field variations can be detected by a component which reacts electrically to changes in magnetic field, such as a Hall Effect device. Increased effectiveness would result from a configuration of several Hall Effect probes for improved magnetic scanning. The Hall probe(s) would be connected to a single electronic instrument. Input to that instrument's computer chip would be in the form of the field magnitudes from which magnetic field ratios could be compared with a known data base obtained from an appropriate manikin mockup. The computer will scan the magnetic field data and make the necessary computations for a number of uses. For example, it can differentiate between correct and incorrect orientations of the internal magnet, or it can register its movements as when the patient breathes (waking or sleeping), eats, or speaks. Such operation is especially critical to the preceding embodiment, since it can register that the pill magnet 17 has indeed "locked into" the correct position and orientation to ensure that it will be attracted by the external magnet 8, so as to prevent airway closure. Simple solid state circuitry 20, in FIG. 8, empowered by a small battery, then triggers a visual display, such as a small light, or a numerical liquid crystal indication, or an audible one, such as a beep. That response is provided by the indicator 21 placed in the neckband 9. Such an indication is then used as a guide for adjusting the neckband into an optimum position. In addition, it can provide monitoring of other data for other dynamic factors during sleeping, breathing, swallowing, speaking, etc., which also can be registered in the readout mechanism.

With the availability of such electronic sensing as a starting point, additional information can be monitored as a result of the movement of the magnetic element(s) in the body for any of the preceding embodiments. Natural movements associated with airway functions, such as breathing, swallowing, speaking, etc. can be motivated. In this manner, the onset of a potential apneaic attack, for example, can be foreseen and observed. In this manner, the invention becomes more than a mere passive restraint against airway closure; it becomes, in addition, an information gathering means.

While the above descriptions contain many specificities, these should not be construed as limitations on the scope of the invention, but rather as exemplifications of preferred embodiments thereof. Many other variations are possible.

For example, all the embodiments can be applied to many living passageways for fluids in humans and animals, in addition to the airway.

Also, while the embodiments given here describe systems employing two, three, or four magnets, all of which are deployed to provide mechanical forces acting on living tissue by the agencies of magnetic attracting or repelling forces, stabilized by auxiliary magnets where required, there is no reason not to employ more magnets than this to cope with more complex requirements. For example, the forces may be required in four positions around a passageway, rather than two, as shown in the described embodiments.

Also, the removable inserted magnet, which is swallowed by the patient as though it were a pill and retained by an attached thread, can be otherwise inserted and retained. For example, it can be inserted with a catheter through a body aperture and itself removed by inserting another magnet to which it will attach itself.

Also, where magnet implantation in the inner wall of a passageway has been described, there are instances wherein implantation in the outer wall or within the wall near or at its center, may be preferable and would not interfere with magnet action in eliminating passageway collapse and closure. Also, in some cases, surgical implantation may not be necessary at all, since the magnet will exert desired forces in the desired direction if it is merely placed adjacent to a passageway wall.

Also, to prevent undesired movements of magnets as a result of exposure to strong magnetic fields (an unlikely possibility), magnets may be surrounded, except for selected small active zones, with magnetic shielding material, such as sheaths of iron foil.

The above-described method and device will eliminate the dysfunction known as sleep apnea and is also applicable to alleviation of other human and animal ailments also caused by undesired involuntary closure of passageways.

At the same time, it is so gentle and benign in action as in no way to affect other normal functions which that passageway engages in. In addition to unobtrusively eliminating sleep apnea breathing dysfunction, it causes no observable changes in normal swallowing, either liquid or solid food, speaking or singing.

Once the magnet is in place and the surgery healed, the patient will not be aware, by reason of pain or perceptible forces, that the implant is in place.

The magnets must resist demagnetization with time or with exposure to counter polarity magnetic fields. Therefore, magnets with high coercive force ratings should be used, such as state of the art rare earth high energy product magnets.

An embodiment has been described which requires no surgery, whatever, in that the magnet will be inserted daily at bedtime, in a required location in the body through an external conduit, such as the mouth. It will be easily retrieved each morning for reinsertion before retiring the next night.

The method and device requires no active powering systems (other than if an instrumentation option is employed). Thus, there will be no requirement for attachment to an electric power source outlet and no moving parts, as with a motor or pump, and thus, no noise or vibration.

In other applications, the magnets can be inserted through a body aperture, like the vagina, the rectum, or the urinary passage, or into a blood vessel with a catheter or other such instrument, and disposed exactly in the location where the passageway closure is required to be prevented. It will be fixed in place with the correct pole orientation for either attractive or repulsive forces by the presence of other magnets. These may be either of the nature of an external attached magnet, or by an already implanted magnet or magnets. When the time comes to remove the magnet, the catheter, now bearing another magnet of suitable opposing polarity, will cause the inserted magnet to be attached to itself by virtue of its magnet force, greater than any other magnetic forces in that locality, and as the catheter is withdrawn, the inserted magnet will be withdrawn with it. Other means to clasp the magnet for withdrawal may comprise hooks or pincers.

In the embodiments described herein, at least two magnets are disposed adjacent an air passageway consisting of tubular walls of tissue. At least one region of the wall tissue is relatively soft and flabby with the resultant possibility that when not tensed, it can move inwardly, closing the air passageway. The magnets provide magnet fields which react with each other to either repel or attract the magnet adjacent the soft tissue. In one embodiment, a magnet is implanted in the soft tissue and is therefore outwardly adjacent the soft tissue. In another embodiment, the magnet is suspended in the air passageway and is radially inwardly of the soft tissue. In each of these above two embodiments, a second external magnet may be used to exert an attractive force, preventing closure.

Alternatively, where the first magnet is implanted, a second magnet implanted in a region of hard airway tissue may be employed to exert a repulsive force preventing closure. The term "adjacent", therefore, is intended to encompass magnets which are disposed in, or external to, tissue.

V. Prevention of Accidental Extubation

Figure 9:
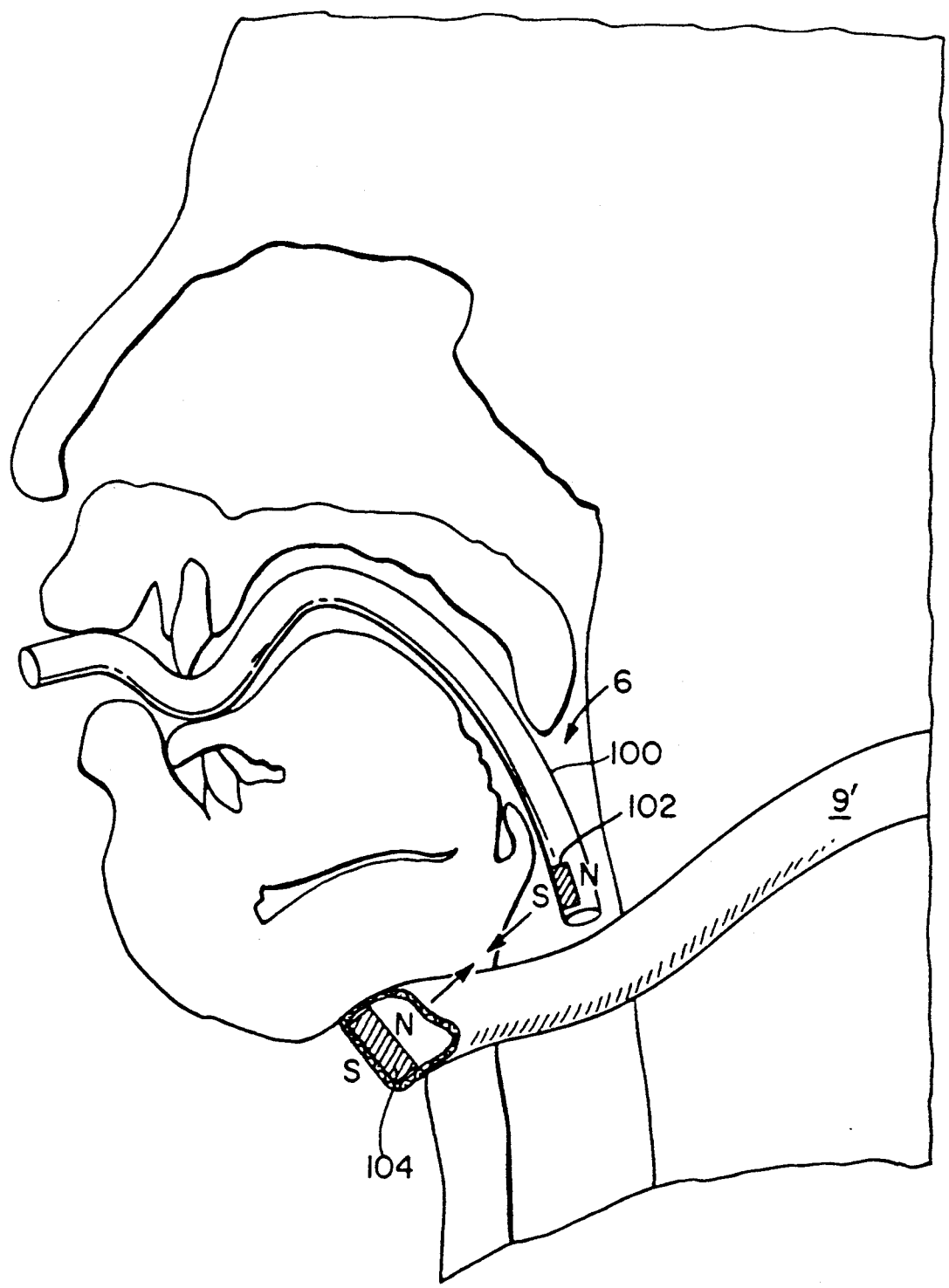
FIG. 9 is a schematic sectional view of an embodiment in which a patient fitted with an endotracheal tube with magnets is shown.

A new way to use magnets for attachment is shown in FIG. 9. It is for the special case in which a tube 100 is inserted into the throat of a patient having difficulty breathing due to involuntary closing of the upper airway. The patient now breathes through the tube 100. It is known as an endotracheal tube. There is a problem in that the tube has a tendency to slip out of the throat (accidental extubation). It is conventional practice to prevent this by incorporating the exterior of the tube to a structure which surrounds the mouth. That structure is fitted with straps which fasten to the patient's head with straps over the top of the skull and around the neck—a very awkward and uncomfortable arrangement. A way to achieve stability of tube position is with attaching magnets 102 and 104.

In FIG. 9, endotracheal tube 100 is shown inserted into oral airway 60 down to the combined upper airway passage 6. Magnet 102 is imbedded into a wall of endotracheal tube 100 at the distal end and oriented so that it faces a position taken up by magnet 104 on neckband 9'. Magnet 104, having opposing polarity to that of magnet 102, will attract magnet 102 and secure it so that tube 100 is not subject to extubation.

Equivalents

Although only preferred embodiments have been specifically described and illustrated herein, it will be appreciated that many modifications and variations of the present invention are possible, in light of the above teachings, and within the purview of the following claims, without departing from the spirit and scope of the invention.

What is claimed is:

1. Apparatus for preventing apnea which involves involuntary closure of an airway passageway in the body of humans and animals in the vicinity of the larynx or pharynx in which the airway consists of tubular airway walls of tissue wherein at least one first region of said wall tissue is relatively soft and movable and one second region of said wall tissue opposite said first region is relatively rigid, said apparatus comprising:
   a) a first magnet adapted to be disposed external to said body and adjacent said first region for generating a first magnetic field within said passageway;
   b) a second magnet of a size and shape to be implanted within said first region of said passageway in adjacent proximity to said second region for generating a second magnetic field which reacts with said first field to exert a force against said first region which acts in a direction away from closure of said passageway.

2. The apparatus of claim 1 including means for holding the first magnet against the soft tissue of the first region.

3. Apparatus in accordance with claim 2, wherein a surface of the second magnet faces a surface of the first magnet and is of opposite magnetic polarity to the surface of the first magnet.

4. The apparatus of claim 1 wherein the first and second magnet is formed of material having an energy product in the range from 18 to 35 million gauss/oersted.

5. The apparatus of claim 1 wherein the second magnet is coated with a biocompatible polymer.

6. Apparatus in accordance with claim 1 which includes an externally attached electronic sensing and instrumentation system including electronic circuit means for sensing, which reacts to variations in magnetic fields generated by said first and second magnets, such that monitoring of magnet movement, as a result of passageway movement, can be quantitatively observed and utilized, and a determination made that the magnets are locked into their desired locations and orientation.

7. Apparatus in accordance with claim 1 which includes a mechanical extender attached to one of said magnets, so as to enlarge its area of mechanical influence on passageway tissue.

8. Apparatus of claim 7 wherein the extender is made of a tissue-compatible, non-metallic material, not affected by magnetic fields.

* * * * *